United States Patent [19]

Archibald et al.

[11] 4,038,401

[45] July 26, 1977

[54] NOVEL INDOLE DERIVATIVE

[75] Inventors: John Leheup Archibald, Windsor; John Lambert Jackson, Royston, both of England

[73] Assignee: John Wyeth & Brother Limited, Maidenhead, England

[21] Appl. No.: 657,121

[22] Filed: Feb. 11, 1976

[51] Int. Cl.$^2$ .................. A61K 31/40; C07D 471/04
[52] U.S. Cl. .............................. 424/267; 260/293.61
[58] Field of Search .................. 260/293.61; 424/267

[56] References Cited

U.S. PATENT DOCUMENTS 3,527,761  9/1970  Archibald et al. .............. 260/293.61

Primary Examiner—John D. Randolph
Attorney, Agent, or Firm—Robert Wiser

[57] ABSTRACT

The invention provides 4-benzamido-1-[4-(indol-3-yl)-4-oxobutyl] piperidine and the pharmaceutically acceptable acid addition salts thereof. The compound and its salts exhibit hypotensive and anti-hypertensive activity.

5 Claims, No Drawings

NOVEL INDOLE DERIVATIVE

The invention relates to a novel indole derivative.

In our U.S. Pat. No. 3,527,761 issued Sept. 8, 1970 we have described a new class of indole derivatives with interesting pharmacological activity.

The class disclosed in U.S. Pat. No. 3,527,761, while exhibiting desirable anti-hypertensive activities does have the drawback of exhibiting a certain level of unwanted side effects such as sedation, upon administration to warm-blooded animals. As with any drug, an important consideration in determining the ultimate clinical usefulness of an anti-hypertensive agent is the relationship of its potency (for its intended purpose) to the dosage at which unwanted side-effects appear, i.e. the therapeutic index.

The chemistry and pharmacology of some of the class of compounds of U.S. Pat. No. 3,527,761 is discussed in J. Med. Chem., 14, 1054–59 (1971). As revealed in this article one of the best members of the series, namely 3-[2(4-benzamidopiperid-1-yl) ethyl]indole (indoramin) has undergone intensive pharmacological investigation. Indoramin exhibits sustained hypotensive action and is undergoing clinical trials as a cardiovascular agent. We have now found that a further compound which is within the Markush expression in U.S. Pat. No. 3,527,761 (though not exemplified) but outside the narrower class discussed in the J. Med. Chem. article possesses an unexpected and surprising superiority in therapeutic index compared to the invention of U.S. Pat. No. 3,527,761, and in fact compared even to the clinically important compound Indoramin. This compound is 4-benzamido-1-[4-(indol-3-yl)-4-oxobutyl]-piperidine, and for example has hypotensive and anti-hypertensive activity which is comparable to that of indoramin but has the advantage of being much less toxic and much less sedative in tests in laboratory animals.

The results may be summarised as follows:

| Toxicity | LD$_{50}$ | data in mice compound mg/kg | |
|---|---|---|---|
| Oral | | Indoramin | 4-benzamido-1-[4-(indol-3-yl)-4-oxobutyl] piperidine |
| 24 hours | | 1320 | >4000 |
| 7/14 days | | 1048 | >4000 |
| Intraperitoneal | | | |
| 24 hours | | 453 | 1002 |
| 7/14 days | | 453 | 542 |

SEDATION

Sedation was measured in rats for Indoramin and 4-Benzamido-1-[4-(indol-3-yl)-4-oxobutyl]piperidine in comparison with the tranquillisers perphenazine and haloperidol which were rated at 10.

METHOD

Twelve rats of each type were split into groups of three and dosed orally with 10, 25 or 50 mg/kg of the test compound in a vehicle comprising hydroxymethylcellulose (0.5%) in (0.9% saline). Each rat was housed singly, after dosing and observed closely for 2 hours, then intermittently for a further four hours, behavioural changes being noted.

The animals were left at least 72 hours before re-dosing to ensure the disappearance of residual hypotensive and sedative effects.

| | Results | |
|---|---|---|
| | Compound Increase in comparative sedation | |
| Strain (rats) | Indoramin | 4-benzamido-1-[4-(indol-3-yl)-4-oxobutyl] piperidine |
| Normotensive | | 1 |
| Spontaneously hypertensive | 7 | 1 |
| Renal hypertensive | 4 | 2 |

The sedative potential of the compounds was also compared in the Patas monkey at dosing levels of 10–100 mg/kg. A group of 6 animals were housed singly and observed daily for one week prior to dosing them orally with the drugs. Each animal served as its own control because of individual variation in temperament. An assessment was made of behavioural changes (indicative of sedation) induced by either drug and the dose ratio separating the drug effects on identical features was determined.

The relative sedation potencies of the drugs in the two animal species rat and monkey are summarised below.

| Species | Approximate sedative potency ratio | | Duration of sedation 50 mg/kg | |
|---|---|---|---|---|
| | 4-benzamido-1-[4-(indol-3-yl)-4-oxo-butyl]-piperidine | Indoramin | 4-benzamido-1-[4-(indol-3-yl)-4-oxo-butyl]-piperidine | Indoramin |
| Normotensive rat (male and female | 1 | 5 | 6 hrs | 24–28 hrs |
| Spontaneous hypertensive rat (male) | 1 | 5 | 6 hrs | 6 hrs |
| Renal hypertensive rat (female) | 1 | 5 | 6 hrs | 6–24 hrs |
| Patas Monkey (male) | 1 | 5 | 4–6 hrs | 24–28 hrs |

Accordingly the invention provides 4-benzamido-1-[4-(indol-3-yl) -4-oxobutyl]-piperidine and the acid addition salts thereof.

The acid addition salts include the hydrochloride, hydrobromide, sulphate, nitrate, phosphate, sulphonate (such as the methane-sulphonate and p-toluene-sulphonate), acetate, maleate, fumarate, tartrate, formate or salts of any other pharmaceutically acceptable organic or inorganic acid.

The compound of the present invention may be prepared by any of the methods described in U.S. Pat. No. 3,527,761 preferably by reacting a 3-(4-halobutyryl)indole with 4-benzamidopiperidine with conversion to an acid addition salt if desired.

The invention includes pharmaceutical compositions comprising a compound of the invention and a pharmaceutically acceptable carrier. It also includes a method for producing an anti-hypertensive effect without sedation in a warm-blooded animal which comprises administering an anti-hypertensive amount of the compound 4-Benzamido-1-[4-(indol-3-yl) -4-oxobutyl]-piperidine or a pharmaceutically acceptable acid addition salt thereof.

In practising the method aspects of producing an anti-hypertensive effect without sedation in warm-blooded animals, the compositions can be administered in a variety of dosage forms, either orally or parenterally. The dosage requirements will vary with particular composition being employed, thus the severity and nature of the hypertension, and the animal being treated. With large animals (about 70 kg. body weight), by the oral route the dose is from about 10 to about 500 mg., and preferably from about 25 to about 250 mg., every four hours, or as needed. By the parenteral route, the dosage is from about 2 to about 150 mg. as needed. Ideally therapy should be initiated with lower dosages, the dosages thereafter being increased until the desired anti-hypertensive effect is obtained.

Anti-hypertensive activity is determined by the following procedure:

Male or female rats are rendered hypertensive by applying a figure of 8 ligature around one kidney and contralateral nephrectomy. Blood pressure stabilises at a hypertensive level after 6 weeks. Systolic pressure is measured indirectly using an E and M Pneumatic Tail Pulse Transducer and a Devices M2 recorder. A control group of rats is run with each group reacted with drug. Each group usually consists of six rats. Drugs are usually administered by the IP or oral routes. Pressures are read prior to drug administration and at 2 and 24 hours thereafter.

Results for a comparative test run with Indoramin and the compound of the invention are given below:

Blood pressure is expressed as % of control values at x hours after an oral dose of 25 mg/kg. In the test 12 rats were used instead of the usual 6.

|  | Indoramin | 4-benzamido-1-[4-(indol-3-yl)-4-oxobutyl]-piperidine |
|---|---|---|
| X = 2 | 78.0 | 60.9 |
| X = 6 | 76.0 | 62.0 |
| X = 24 | 98.0 | 99.0 |

The compound of the invention may be formulated into pharmaceutical compositions which may be micronised. In addition to the active ingredient, said compositions also contain a non-toxic carrier. Any suitable carrier known in the art can be used to prepare the pharmaceutical compositions. In such a composition, the carrier may be a solid, liquid or mixture of a solid and a liquid. Solid form compositions include powders, tablets and capsules. A solid carrier can be one or more substances which may also act as flavouring agents, lubricants, solubilisers, suspending agents, binders, or tablet-disintegrating agents; it can also be an encapsulating material. In powders the carrier is a finely divided solid which is in admixture with the finely divided active ingredient. In tablets the active ingredients are mixed with a carrier having the necessary binding properties in suitable proportions and compacted in the shape and size desired. The powders and tablets preferably contain from 5 to 99, preferably 10–80% of the active ingredient. Suitable solid carriers are magnesium carbonate, magnesium stearate, talc, sugar, lactose, pectin, dextrin, starch, gelatin, tragacanth, methyl cellulose, sodium carboxymethyl cellulose, a low melting wax, and cocoa butter. The term "composition" is intended to include the formulation of an active ingredient with encapsulating material as carrier to give a capsule in which the active ingredient (with or without other carriers) is surrounded by carrier, which is thus in association with it. Similarly cachets are included.

Sterile liquid form compositions include sterile solutions, suspensions, emulsions, syrups and elixirs. The active ingredient can be dissolved or suspended in a pharmaceutically acceptable sterile liquid carrier, such as sterile water, sterile organic solvent or a mixture of both. Preferably a liquid carrier is one suitable for parenteral injection. Where the active ingredient is sufficiently soluble it can be dissolved in normal saline as a carrier; if it is too insoluble for this it can often be dissolved in a suitable organic solvent, for instance aqueous propylene glycol or polyethylene glycol solutions. Aqueous propylene glycol containing from 10 to 75% of the glycol by weight is generally suitable. In other instances compositions can be made by dispersing the finely-divided active ingredient in aqueous starch or sodium carboxymethyl cellulose solution, or in a suitable oil, for instance arachis oil. Liquid pharmaceutical compositions which are sterile solutions or suspensions can be utilised by intramuscular, intraperitoneal or subcutaneous injection. In many instances a compound is orally active and can be administered orally either in liquid or solid composition form.

Preferably the pharmaceutical composition is in unit dosage form. In such form, the composition is subdivided in unit doses containing appropriate quantities of the active ingredient; the unit dosage form can be a packaged composition, the package containing specific quantities of compositions, for example packeted powders or vials or ampoules. The unit dosage form can be a capsule, cachet or tablet itself, or it can be the appropriate number of any of these in package form. The quantity of active ingredient in a unit dose of composition may be varied or adjusted from 5 mg. or less to 500 or more, according to the particular need and the activity of the active ingredient. The invention also includes the compounds in the absence of carrier where the compounds are in unit dosage form.

The invention is illustrated by the following example:

4-Benzamido-1-[4-(indol-3-yl)-4-oxobutyl]piperidine

A mixture of 3-(4-chlorobutyryl)indole (22.2g. 0.1 mol.) and 4-benzamidopiperidine (40.8g. 0.2 mol.) was stirred and heated at 160° C for 1 hour. The melt was cooled and extracted under reflux with water (200 ml.) for 0.5 hour. The insoluble granular residue was collected by filtration and crystallised from a mixture of ethanol (150 ml) and water (50 ml.), with charcoal treatment, to yield the title compound (15.5 g. 40%). The hydrochloride was precipitated from a solution of the base, in ethanol by addition of ethanolic hydrogen chloride (16.2 g. 38%) m.p. 275–6° C. $C_{24}H_{27}N_3O$. HCl $\frac{1}{4}H_2O$ requires C, 67.0 H, 6.7; N, 9.8 Found: C, 67.0; H, 6.7; N, 9.7%. It can also be precipitated from a solution of the base in dimethylformamide by addition of ethanolic hydrogen chloride and propan-2-ol. This gives the anhydrous form of the title compound hydrochloride m.p. 285.5° C.

Anal. $C_{24}H_{27}N_3O$, HCl requires C, 67.67; H, 6.63; N, 9.86. Found: C, 67.56; H, 6.68; N, 9.74.

We claim:

1. 4-Benzamido-1-[4-(indol-3-yl)-4-oxobutyl]-piperidine or a pharmaceutically acceptable acid addition salt thereof.

2. 4-Benzamido-1-[4-(indol-3-yl)-4-oxobutyl]-piperdine hydrochloride.

3. A pharmaceutical composition comprising a compound as claimed in claim 1 and a pharmaceutically acceptable carrier.

4. A pharmaceutical composition as claimed in claim 3 in unit dosage form.

5. A method for producing an anti-hypertensive effect without sedation in a warm-blooded animal which comprises administering an anti-hypertensive amount of the compound 4-benzamido-1-[4-(indol-3-yl)-4-oxobutyl]-piperidine or a pharmaceutically acceptable acid addition salt thereof.

* * * * *